US00PP23651P3

(12) United States Plant Patent
Yencho et al.

(10) Patent No.: US PP23,651 P3
(45) Date of Patent: Jun. 4, 2013

(54) SWEETPOTATO PLANT NAMED 'NCORNSP-014BWPI'

(50) Latin Name: ***Ipomoea batatas* (L.) Lam.**
Varietal Denomination: NCORNSP-014BWPI

(75) Inventors: G. Craig Yencho, Raleigh, NC (US); Kenneth V. Pecota, Raleigh, NC (US); Meri K. Reeber, Apex, NC (US)

(73) Assignee: North Carolina State University, Raleigh, NC (US)

( * ) Notice: Subject to any disclaimer, the term of this patent is extended or adjusted under 35 U.S.C. 154(b) by 37 days.

(21) Appl. No.: 13/065,464

(22) Filed: Mar. 22, 2011

(65) Prior Publication Data

US 2012/0246771 P1 Sep. 27, 2012

(51) Int. Cl.
*A01H 5/00* (2006.01)

(52) U.S. Cl.
USPC ..... Plt./258

(58) Field of Classification Search ..... Plt./258
See application file for complete search history.

(56) References Cited

PUBLICATIONS

Office Action from the United States Patent and Trademark Office for U.S. Appl. No. 13/065,468 dated Sep. 10, 2012 (10 pages).
Office Action from the United States Patent and Trademark Office for U.S. Appl. No. 13/065,463 dated Sep. 11, 2012 (10 pages).
United States Patent Office Notice of Allowance for U.S. Appl. No. 13/065,468 dated Jan. 16, 2013 (7 pages).
United States Patent Office Notice of Allowance for U.S. Appl. No. 13/065,463 dated Jan. 14, 2013 (6 pages).

*Primary Examiner* — June Hwu
(74) *Attorney, Agent, or Firm* — Michael Best & Friedrich LLP

(57) ABSTRACT

'NCORNSP-014BWPI' is new and distinct variety of ornamental sweetpotato. 'NCORNSP-014BWPI' is an erect to semi-erect, bunch-type cultivar producing many short shoots. This ornamental sweetpotato variety is distinguishable from other cultivars by its toothed to slightly-lobed dark purple leaves, a compact habit and semi-erect mounding plant architecture. 'NCORNSP-014BWPI' has a very good vigor, is very well branched and is well suited for production as a landscape or containerized plant. The production of flowers by 'NCORNSP-014BWPI' is absent, even under short day conditions.

3 Drawing Sheets

Latin name of the genus and species: *Ipomoea batatas* (L.) Lam.

Variety denomination: 'NCORNSP-014BWPI'.

BACKGROUND

*Ipomoea batatas* is a member of the morning glory family Convolvulaceae. This species is grown worldwide and exhibits a wide range of plant forms and colors. The cultivated members of *Ipomoea batatas* that are grown by farmers are commonly produced for consumption of their enlarged storage roots. Such types typically produce a fast growing green vine that has a wide variety of leaf shapes ranging from palmate and deeply lobed, to cordate or triangular shaped leaves with no lobes.

*Ipomoea batatas* ornamental sweetpotato plants, like their edible forms, are a heat-loving, drought tolerant, perennial vine, typically grown as an annual. However, ornamental sweetpotato plants are distinguished from the edible cultivated forms in that they possess unique foliage colors, leaf shapes, and growth habits, which have significant value in the ornamental marketplace.

Ornamental sweetpotato plants are desirable in the landscape and ornamental industries because their foliage comes in a wide variety of colors (e.g. pale yellow to dark purple with some exhibiting temporal and individual leaf color variegation patterns) and plant shapes (e.g. mounded and very compact to prostrate and highly spreading). They can be grown in a potted plant and/or mixed planting format, and they have the ability to cover a large space or hang over walls and decorative pots creating brightly colored and textured backdrops in gardens and patios. Most ornamental sweetpotatoes grow and last the entire growing season and they require little maintenance. Moreover, these plants have few insect or disease problems.

Applicants desire to produce new cultivars of ornamental sweetpotato with new or improved foliage colors, variegation patterns, leaf shapes, and plant architectures. In addition, applicants believe it would be advantageous to develop cultivars of ornamental sweetpotato exhibiting a more compact growth that do not out-compete other species in mixed containers.

'NCORNSP-014BWPI' addresses at least one of the above-noted problems.

Lineage. 'NCORNSP-014BWPI' (breeding designation NC6881-044RN) originated from open pollinated seed harvested from the proprietary *Ipomoea batatas* breeding line NC5309-019ORN (the female parent; not patented). Botanical seed was harvested from this and other ornamental sweetpotato lines planted in our summer advanced ornamental replicated trials between June of 2008 and November of 2008. The breeding line NC309-019ORN resulted from a conventional cross between NC1925-0350RN and NC2500-0220RN (proprietary breeding lines; not patented). Botanical seed from this half-sib family were planted in the greenhouse during February 2009. The first cycle of selection on the population was exercised in the seedling trays and survivors were transferred to a single 6-inch pot, which was then maintained in the greenhouse. Cuttings (2 each) were taken from the plants in May and planted in the field as 2-plant unreplicated plots during early July 2009. The single, individual plant now known as 'NCORNSP-014BWPI' was selected Aug. 19, 2009 because of its combination of exceptional features, and has been propagated asexually in Raleigh, N.C. since that time.

Asexual Reproduction. Since its selection, 'NCORNSP-014BWPI' has been asexually reproduced in Raleigh, N.C. predominantly by vegetative propagation of vine cuttings. Successively, there have been two cycles of vegetative propagation, one cycle of tissue culture micropropagation, and multiple vegetative propagation cycles to increase the plant population. Asexual reproduction of 'NCORNSP-014BWPI' by cuttings has shown that the unique features of the new cultivar are stable and the plant reproduces true-to-type in successive generations.

REFERENCE TO PLANT BREEDERS RIGHTS

Plant Breeders Rights for 'NCORNSP-014BWPI' have not been applied for. 'NCORNSP-014BWPI' has not been made publicly available or sold more than one year prior to the date of this application.

SUMMARY

'NCORNSP-014BWPI' is an erect to semi-erect, bunch-type, ornamental sweetpotato variety producing many short shoots. This variety is distinguishable from other cultivars by its dark purple, toothed to slightly lobed leaves; a compact plant habit and erect to semi-erect mounding plant architecture. The distinctly toothed feature of the leaves of this plant and the plant architecture make 'NCORNSP-014BWPI' unique amongst the current ornamental sweetpotatoes in the marketplace. 'NCORNSP-014BWPI' also exhibits very good vigor and is well branched. In greenhouse and field trials conducted by the breeding program and industry collaborators during 2009 to present 'NCORNSP-014BWPI' has been shown to be much less vigorous than *Ipomoea batatas* 'Margarita' and 'Blackie' making this variety more suitable for use as a landscape or containerized plant. 'NCORNSP-014BWPI' does not produce flowers, even under short day conditions.

BRIEF DESCRIPTION OF THE DRAWINGS

The photographs in the drawings were made using conventional techniques and show the colors as true as reasonably possible by conventional photography. Colors in the photographs may differ slightly from the color values cited in the detailed botanical description, which accurately describe the colors of the new *Ipomoea batatas*.

DETAILED DESCRIPTION OF THE NEW VARIETY

The following is a detailed description of the botanical characteristics of a new and distinct cultivar of *Ipomoea batatas* plant known by the cultivar name 'NCORNSP-014BWPI'.

All colors cited herein refer to *The Royal Horticultural Society Colour Chart* designations (The Royal Horticultural Society, London, 2007, 5$^{th}$ ed.) except where general terms of ordinary dictionary significance are used. Plant descriptions are based on the standardized international sweetpotato descriptors established jointly by the International Potato Center (CIP), Lima, Peru; The Asian Vegetable Research and Development Center (AVRDC), Taipei, Taiwan; and the International Board for Plant Genetic Resources (IBPGR), Rome, Italy (CIP, AVRDC, IBPGR. 1991. Descriptors for Sweet Potato. Huaman, Z., editor. International Board for Plant Genetic Resources, Rome, Italy, 134 pp.). Where dimensions, sizes, colors, and other characteristics are given, it is to be understood that such characteristics are approximations or averages set forth as accurately as practicable.

The descriptions reported herein are from 62-day-old specimens grown individually in six-inch azalea pots. The plants were grown in Raleigh, N.C., under commercial practice in a glass-covered greenhouse, where, during the fall, day and night temperatures range between 18-30° C. and 15-21° C., respectively. Plant ratings were taken during the last week of November 2010. 'NCORNSP-014BWPI' has not been observed under all possible environmental conditions; therefore, the phenotype may vary with variations in the environment such as season, temperature, light intensity, day length, cultural conditions, and the like.

Classification:

*Botanical name.*—*Ipomoea batatas* (L.) Lam.

*Common name.*—Ornamental Sweetpotato.

*Variety name.*—'NCORNSP-014BWPI'.

Growth conditions: 'NCORNSP-014BWPI' has good vigor, a moderate growth rate, and is very adaptable to container culture. In locales with mild winter conditions, *Ipomoea batatas* 'NCORNSP-014BWPI' will grow perennially; otherwise it is an annual plant. Similar to cultivated sweetpotatoes, wind or rain rarely causes much damage to 'NCORNSP-014BWPI', but if damage does occur, the plant drops the damaged leaves and grows new shoots at nodes where the leaves were lost. Under low light levels in a greenhouse, 'NCORNSP-014BWPI' can develop intumescence, which will remain on the affected foliage, but will be outgrown with new foliage.

Figure 1:
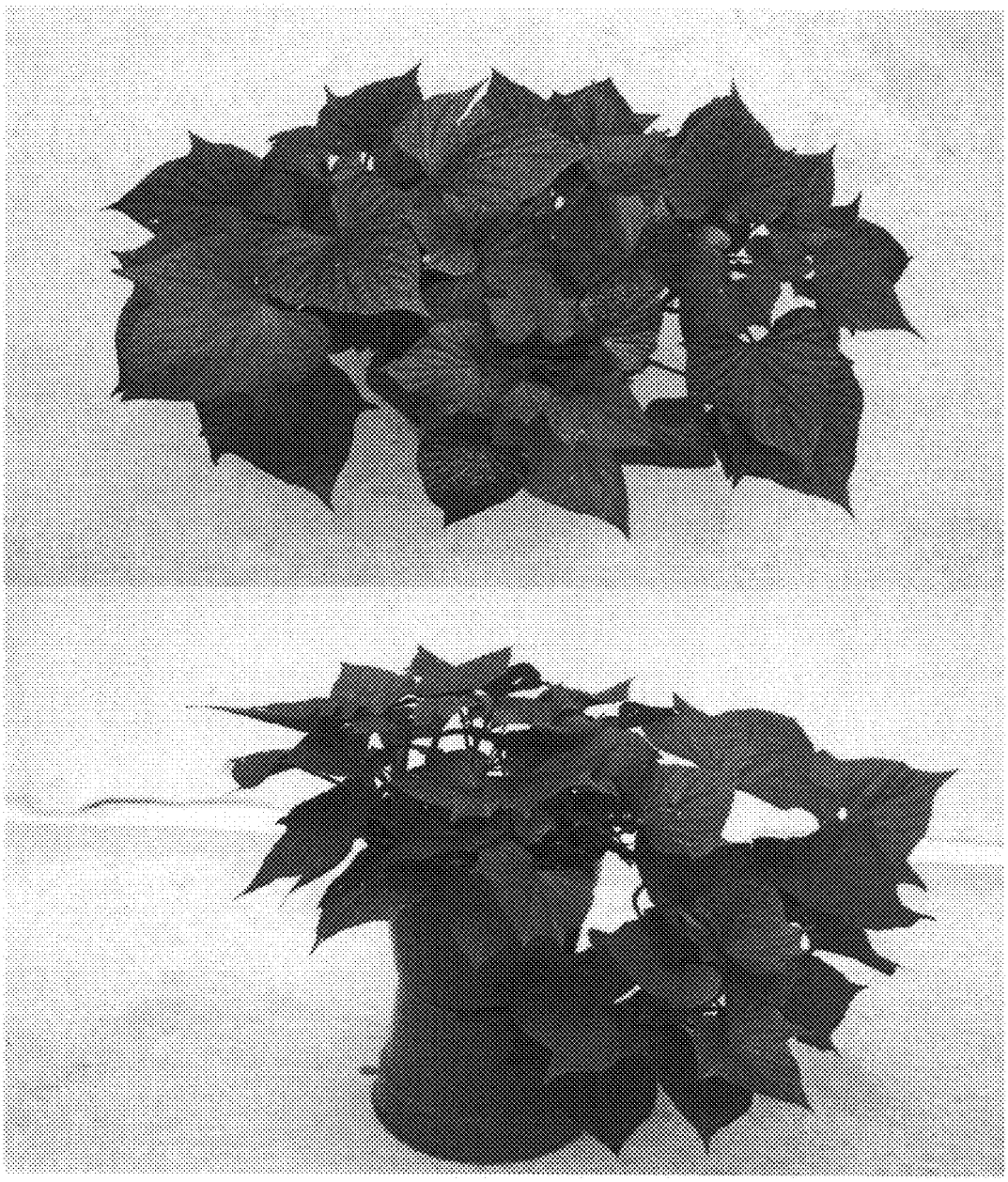
FIG. 1 is a color photograph of a typical specimen of greenhouse grown *Ipomoea batatas* 'NCORNSP-014BWPI' in a 6-inch pot from the side and top, 84 days after planting.
Figure 2:
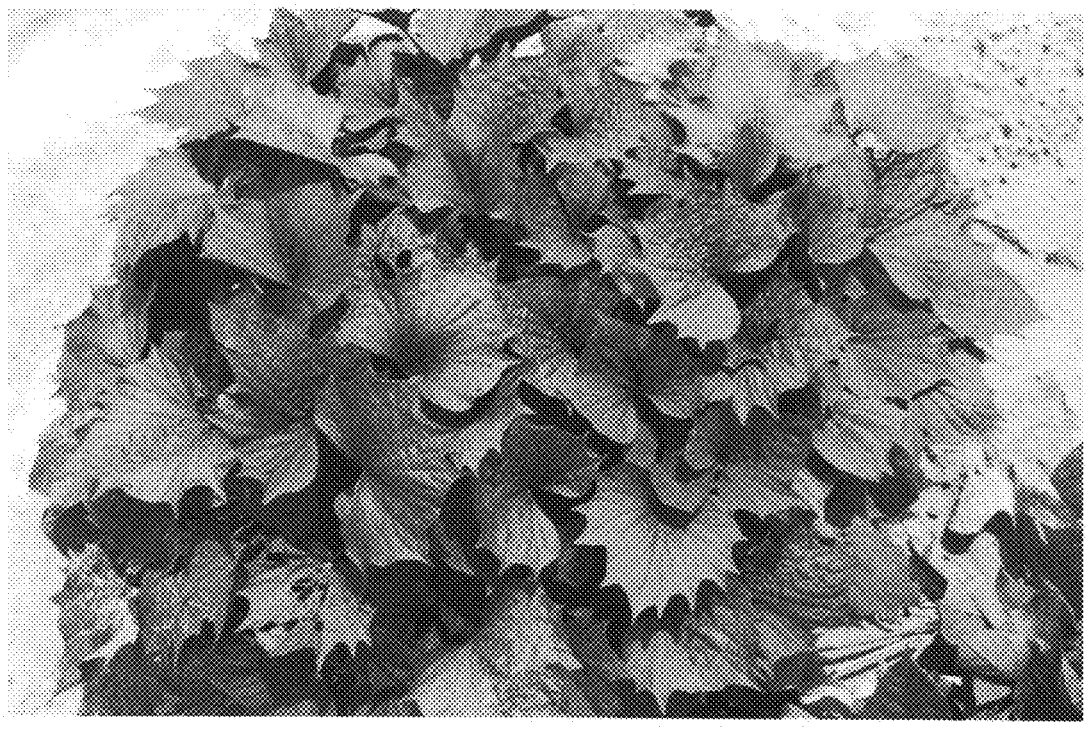
FIG. 2 is a color photograph of a typical specimen of *Ipomoea batatas* 'NCORNSP-014BWPI' from the top in the field, 64 days after planting.
Figure 3:
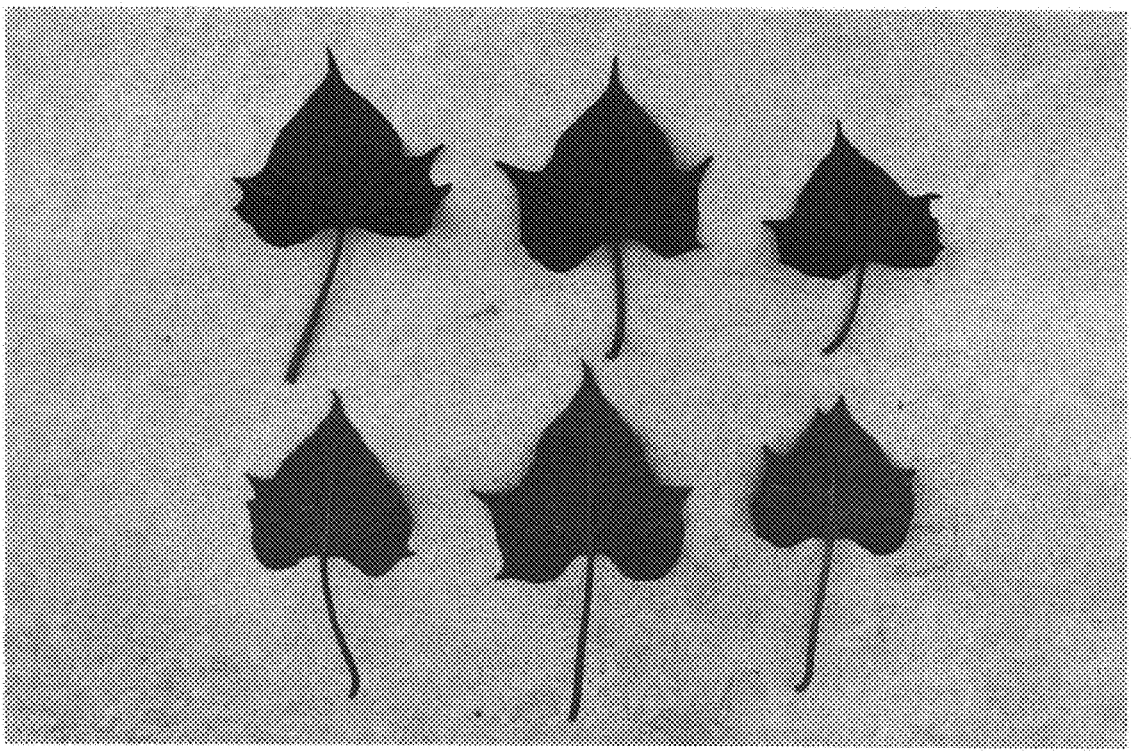
FIG. 3 is a color photograph showing the variety of leaves produced by *Ipomoea batatas* 'NCORNSP-014BWPI' 84 days after planting.

Aboveground structure and coloration: FIGS. 1 and 2 show the shape and coloration of a typical specimen of 'NCORNSP-014BWPI'. Color will vary somewhat due to temperature and nutrient stress, which affect the anthocyanin pigments that produce the purple color. Overall, this cultivar is a round, compact, mounded, spreading herbaceous plant that has an average height of 19.4 cm and an average area of spread of 39.8 cm. The growth habit of this plant is to grow upright with shoots growing outward.

Branches:

*Branching habit.*—Freely-branching with ~4 lateral branches coming off the stem. Very dense foliage and no pinching is required to stimulate branching.

*Vegetative lateral branches.*—Length: ~17.4 cm. Diameter: ~0.5 cm. Internodes are short with an average length of ~1.2 cm. Many lateral branches are formed and each axil has latent shoots.

*Stem.*—Round and glabrous, with an outward and upward bending aspect, with very strong, slightly flexible, non-brittle strength. Color: Dark Purple (RHS N77A).

*Petiole.*—Length: ~9.5 cm. Diameter: ~0.4 cm. Color: Dark Purple (RHS N79B). Texture: slightly pubescent.

Foliage: Leaves are alternate and tend to spiral around the stem. They are simple and cordate to triangular with irregular projecting points (i.e. teeth). Leaf texture is glabrous and matte on both the upper and lower surface. Leaf shape is somewhat variable as is leaf size (see FIG. 2).

*Quantity.*—Heavily foliated, with — 17 leaves per lateral branch.

*Mature leaf length.*—~12.7 cm.

*Mature leaf width.*—~17.8 cm.

*Leaf margin.*—Dentate to serrate.

*Centra/lobe width.*—~7.3 cm.

*Centra/lobe length.*—~6.3 cm.

*Mid-vein lobe length.*—~6.6 cm.

*Mid-vein lobe width.*—~1.4 cm.

*Centra/lobe shape.*—Deltoid.

*Two axillary lobes.*—Palmate both shallowly deltoid.

*Leaf apex.*—Deltoid.

*Leaf base.*—Cordate.

*Leaf.*—Glabrous texture and matte finish.

*Venation.*—Palmate at the base with arcuate veins in the center lamina.

*Color.*—Leaves transition from purple to dark purple as they mature. See also Table 1.

TABLE 1

| Leaf Structure | Upper Surface | Lower Surface |
|---|---|---|
| Young Leaf | Purple, 187A | Purple, N1 86C |
| Mature Leaf | Dark Purple, N1 86A with a dark green base, N137A | Purple, N1 86C |
| Vein- mature leaf | 187A | N79B |
| Vein- young leaf | N77A with 147A base | N77A with 147C |

Flowers: The production of flowers by 'NCORNSP-014BWPI' is absent even under short day conditions.

Storage root coloration: Plants form no, to very small, underground storage roots that are highly malformed and do not meet USDA Sweetpotato Storage Root Grade Standards. Storage roots that do form typically possess purple colored skin (N79A) and a yellow cream (162B) flesh color.

Comparison with other *Ipomoea batatas* cultivars: 'NCORNSP-014BWPI' is very distinct based on leaf color, leaf shape, and plant architecture. Of the common cultivars of ornamental sweetpotato, 'NCORNSP-014BWPI' is best compared with the 'Sweet Caroline Bewitched cultivar (Table 2). Like 'Sweet Caroline Bewitched', 'NCORNSP-014BWPI' has purple leaves. However, the leaves of 'NCORNSP-014BWPI' are smaller, darker purple, and are more deeply lobed than those of 'Sweet Caroline Bewitched'. 'NCORNSP-014BWPI' has purple immature leaves compared with the green immature leaves of 'Sweet Caroline Bewitched'. 'NCORNSP-014BWPI' has a compact, semi-upright, mounding plant habit compared with the upright habit of 'Sweet Caroline Bewitched'. Furthermore, 'NCORNSP-014BWPI' has a more uniform toothing habit as compared with the more irregular teeth of 'Sweet Caroline Bewitched'. Unlike 'Sweet Caroline Bewitched', which occasionally produces flowers, 'NCORNSP-014BWPI' will not produce flowers, even under short day conditions.

TABLE 2

| Characteristic | 'NCORNSP-014BWPI' | Female Parent 'NC5309-019ORN' | 'Sweet Caroline Bewitched' |
|---|---|---|---|
| Plant Habit | Compact, Semi-Upright | Compact, Semi-Upright | Compact, Upright |
| Foliage Color | Dark purple (RHS N186A) | Dark purple (RHS N186A) | Purple (RHS 137A, N92A) |
| Leaf Size | Moderate-Large | Moderate | Large |
| Leaf Shape | Slightly lobed, toothed | Moderately Lobed | Irregular, toothed |

Disease or pest resistance: 'NCORNSP-014BWPI' is susceptible to Sweetpotato Feathery Mottle Virus and damage by Japanese beetles. Its resistance or susceptibility to other known insects and pathogens of sweetpotato is unknown.

We claim:

1. A new and distinct cultivar of *Ipomoea batatas* ornamental sweetpotato plant named 'NCORNSP-014BWPI', substantially as illustrated and described herein.

* * * * *